(12) United States Patent
Collier

(10) Patent No.: US 10,306,849 B2
(45) Date of Patent: Jun. 4, 2019

(54) HYBRID VARIETY H1307

(71) Applicant: H.J. Heinz Company Brands LLC, Pittsburgh, PA (US)

(72) Inventor: George Collier, Wheatley (CA)

(73) Assignee: H.J. Heinz Company Brands LLC, Pittsburgh, PA (US)

( * ) Notice: Subject to any disclaimer, the term of this patent is extended or adjusted under 35 U.S.C. 154(b) by 0 days.

(21) Appl. No.: 15/392,765

(22) Filed: Dec. 28, 2016

(65) Prior Publication Data

US 2017/0105377 A1    Apr. 20, 2017

Related U.S. Application Data

(62) Division of application No. 14/690,278, filed on Apr. 17, 2015, now Pat. No. 9,861,046.

(60) Provisional application No. 61/993,537, filed on May 15, 2014.

(51) Int. Cl.
  *A01H 5/08*   (2018.01)
  *A01H 1/00*   (2006.01)
  *A01H 1/02*   (2006.01)
  *A01H 6/82*   (2018.01)

(52) U.S. Cl.
  CPC ............... *A01H 5/08* (2013.01); *A01H 1/02* (2013.01); *A01H 6/825* (2018.05)

(58) Field of Classification Search
  None
  See application file for complete search history.

(56) References Cited

U.S. PATENT DOCUMENTS

| | | | |
|---|---|---|---|
| 7,932,441 B2 * | 4/2011 | Bunn | |
| 2013/0086710 A1 | 4/2013 | Schroeder | |
| 2014/0109253 A1 | 4/2014 | Schroeder | |

* cited by examiner

*Primary Examiner* — Phuong T Bui
(74) *Attorney, Agent, or Firm* — Fitch, Even, Tabin & Flannery LLP

(57) ABSTRACT

Hybrid tomato variety 'H1307' is described. The 'H1307' tomato variety is a ground-culture hybrid tomato variety suitable for machine harvest.

11 Claims, 1 Drawing Sheet
(1 of 1 Drawing Sheet(s) Filed in Color)

HYBRID VARIETY H1307

CROSS REFERENCE TO RELATED APPLICATIONS

This application is a divisional of U.S. application Ser. No. 14/690,278, filed Apr. 17, 2015, now U.S. Pat. No. 9,861,046, which claims the benefit of U.S. Provisional Application No. 61/993,537, filed May 15, 2014, which are hereby incorporated by reference in their entireties.

FIELD

This invention relates to the field of plant breeding. In particular, this invention relates to new tomato, *Solanum lycopersicum*, variety denominated 'H1307'.

BACKGROUND

Breeding improved tomato varieties involves providing genetics that give an advantage to the grower, processor, consumer, or other member of the supply chain. The improvement may be in the form of field performance, disease resistance, factory performance, or a fruit quality characteristic. For a tomato variety to be suitable to be grown for processing, the variety must have a concentrated fruit setting and maturity, firm fruit, and sufficient rot tolerance to allow early fruit to remain rot-free while later fruit continues to develop and ripen.

Most commercial processing tomato varieties are hybrids resulting from a cross pollination of two true-breeding, inbred parents. Through the use of true-breeding lines, a hybrid is produced that often displays characteristics of each parent, and often demonstrates characteristics that are superior to either parent alone, or that allow a hybrid to mask inadequacies of the individual parents.

Processing tomato varieties combining high levels of tolerance to bacterial canker (*Clavibacter michiganense* ssp. *michiganense*), early blight (*Alternaria solani*), and bacterial spot (*Xanthomonas* spp.) are highly desirable in humid climates where these diseases present production issues.

Moreover, in regions such as California, the industry has begun to see a considerable amount of pressure from two particular diseases: tomato spotted wilt virus (TSWV) and *Fusarium oxysporum* pv. *lycopersici* race 3 (*fusarium* wilt race 3). Thus, varieties with resistance to either or both are in high demand by both growers and processors to ensure a productive crop cycle.

An additional important contribution that tomatoes provide to the human diet is the antioxidant lycopene. Specifically, processing tomato varieties are the key form of tomato intake in the US diet. Higher levels of lycopene are beneficial both from a nutritional standpoint and from a consumer perception and quality standpoint. Tomato varieties having higher levels of lycopene result in products with a deeper red color that can be considered an indicator of higher product quality. Thus, a tomato variety with higher levels of lycopene can be valuable from both a nutritional standpoint and a quality standpoint. However, to be commercially viable and useful, the tomato variety must perform acceptably as required by any other processing tomato variety.

SUMMARY

In order to meet these needs, the present invention provides improved tomato variety 'H1307', which has resistance to early blight, bacterial spot, and bacterial canker diseases of tomato coupled with competitive field yield, as compared to industry standard varieties such as 'H3402' and 'H9706'. The variety 'H1307' has resistance to *verticillium* wilt race 1, *fusarium* wilt races 1 and 2, southern root knot nematode, bacterial canker, bacterial spot, and early blight. The fruit of 'H1307' are very firm with an average fruit weight of 81 grams. Tolerance to fruit rot in 'H1307' is good, allowing for once-over machine harvesting applications requiring extended field holding.

The characteristics that determine the quality of tomato fruit used for processing are different from that of tomato fruit used for the fresh market. Processing characteristics are commonly tested on samples of tomato pulp or juice produced in a way that is well known in the art. For example, a fixed mass of tomatoes may be cooked in a microwave oven for several minutes to halt any enzymatic breakdown of the sample, lost water is replaced, and the sample is pulped to remove skin and seeds to produce a uniform juice sample. The juice sample can be analyzed for various quality parameters important to processing tomato including, but not limited to, gross viscosity measurements such as juice Bostwick, soluble solids measurements using a refractometer (°Brix), measurements of acidity and pH, and measurements of color via a Hunter a/b score. The Hunter a/b score is an international industry and USDA standard color measurement of tomato products that provides a representation of the color of the product in a single dimensionless unit. The "a" value represents color on the green to red dimension whereas "b" represents the blue to yellow dimension; a higher a/b ratio is associated with more red color and is often considered a superior product.

Tomato varieties contain varying levels of lycopene (Garcia and Barrett, 2006). Lycopene content of tomato juice can be measured using a protocol developed by Anthon and Barrett (2001), which involves an ethanol/hexane extraction followed by quantification using reflectance at 503 nm.

As used herein, tomato variety 'H1307', tomato plant 'H1307', tomato seed 'H1307', and 'H1307' all refer to the hybrid tomato variety 'H1307', and parts and seeds thereof, having ATCC Accession Number PTA-124119.

In one embodiment, the present invention is directed to tomato seed designated as 'H1307' having ATCC Accession Number PTA-124119. In one embodiment, the present invention is directed to a tomato plant and parts isolated therefrom produced by growing 'H1307' tomato seed. In another embodiment, the present invention is directed to a tomato plant and parts isolated therefrom having all the physiological and morphological characteristics of a tomato plant produced by growing 'H1307' tomato seed having ATCC Accession Number PTA-124119. In still another embodiment, the present invention is directed to an Fi hybrid tomato seed, plants grown from the seed, and leaves, ovules, pollen, tomato fruit, cotyledons, embryos, meristems, anthers, roots, root tips, pistils, flowers, stems, calli, stalks, hypocotyls, and pericarps isolated therefrom having 'H1307' as a parent, wherein 'H1307' is grown from 'H1307' tomato seed having ATCC Accession Number PTA-124119.

Tomato plant parts include leaves, ovules, pollen, tomato fruit, cotyledons, embryos, meristems, anthers, roots, root tips, pistils, flowers, stems, calli, stalks, hypocotyls, pericarps, and the like. In another embodiment, the present invention is further directed to tomato fruit, stems, leaves, parts of leaves, roots, root tips, pollen, ovules, and flowers isolated from 'H1307' tomato plants. In another embodiment, the present invention is further directed to tissue culture or cells derived from 'H1307' tomato plants.

In yet another embodiment, the present invention is further directed to a method of selecting tomato plants by a) growing 'H1307' tomato plants wherein the 'H1307' plants are grown from tomato seed having ATCC Accession Number PTA-124119; and b) selecting a plant from step a). In another embodiment, the present invention is further directed to tomato plants, plant parts and seeds produced by the tomato plants, where the tomato plants are isolated by the selection method of the invention.

In another embodiment, the present invention is further directed to a method of breeding tomato plants by crossing a tomato plant with a plant grown from 'H1307' tomato seed having ATCC Accession Number PTA-124119. In still another embodiment, the present invention is further directed to tomato plants, tomato parts from the tomato plants, and seeds produced therefrom where the tomato plant is isolated by the breeding method of the invention.

BRIEF DESCRIPTION OF THE DRAWING

The patent or application file contains at least one drawing executed in color. Copies of this patent or patent application publication with color drawings will be provided by the office upon request and payment of the necessary fee.

The FIGURE illustrates fruit from tomato variety 'H1307'.

DETAILED DESCRIPTION

'H1307' Tomato Variety

Described herein is a new and distinct tomato varieties named 'H1307' that was developed to provide a ground-culture hybrid tomato variety (i.e., not grown on stakes) that is suitable for machine harvest, and is adaptable to the humid climactic conditions of regions such as Michigan, USA; Ohio, USA; Indiana, USA; Pennsylvania, USA; and southern Ontario, Canada.

Plants of the tomato variety 'H1307' are resistant to *verticillium* wilt race 1, *fusarium* wilt races 1 and 2, root knot nematode, early blight, bacterial spot, and bacterial canker. Additionally, plants of the tomato variety 'H1307' are light green in color with a larger sprawling vine size compared to other tomato varieties of the same market class. Fruit from the tomato variety 'H1307' is firm and has excellent color compared to other tomato varieties of the same market class. Moreover, the tomato variety 'H1307' is adapted to culture in humid growing regions such as the eastern United States and southern Ontario, Canada.

Stability of the 'H1307' Tomato Variety

The tomato variety 'H1307' is uniform and stable within commercially acceptable limits. As is true with other tomato varieties, a small percentage of variants can occur within commercially acceptable limits for almost any characteristic during the course of repeated multiplication. However no variants were observed during the two years in which the variety was observed to be uniform and stable.

Characterization of the 'H1307' Tomato Variety
Seedling
Anthocyanin in hypocotyl of 2-15 cm seedling: Present
Habit of 3-4 week old seedling: Normal
Mature Plant
Growth: Determinate
Form: Normal
Size of canopy: Large
Habit: Sprawling (e.g., decumbent)
Stem
Branching: Profuse (e.g., 'UC82')
Branching at cotyledonary or first leafy node: Present
Number of nodes below first inflorescence: 10 or more
Number of nodes between early (1st-2nd, 2nd-3rd) inflorescences: 1-2
Number of nodes between later developing inflorescences: 1-2
Pubescence on younger: Sparsely hairy (scattered long hairs)
Leaf (Mature Leaf Beneath the 3rd Inflorescence)
Type: Tomato
Morphology of mature leaf: Compound
Margins of major leaflets: Deeply toothed or cut, sps. Toward base
Marginal rolling or wiltiness: Absent
Onset of leaflet rolling: Not Applicable
Surface of major leaflets: Rugose (bumpy or veiny)
Pubescence: Normal
Inflorescence (Observations from 3rd Inflorescence)
Type: Forked
Average number of flowers in inflorescence: 8
Leafy or "running" inflorescences: Absent
Flower
Calyx: Normal, lobes awl-shaped
Calyx-lobes: Shorter the corolla
Corolla color: Yellow
Style pubescence: Sparse
Anthers: All fused into tube
Fasciation (1st flower of 2nd or 3rd inflorescence): Absent
Fruit (3rd Fruit of 2nd or 3rd Cluster)
Typical fruit shape: Blocky
Shape of transverse section: Round
Shape of stem end: Flat
Shape of blossom end: Indented (slight)
Shape of pistil scar: Dot
Abscission layer: Absent (jointless)
Point of detachment of fruit at harvest: At calyx attachment
Average length (in mm) of mature fruit (stem axis): 67.5 mm
Average diameter (in mm) of fruit at widest point: 44.7 mm
Average weight (in g) of mature fruit: 81 g
Number of locules: Two
Fruit surface: Slightly rough
Fruit base color (mature-green stage): Apple or medium green
Fruit pattern (mature-green stage): Uniform green
Fruit color, full-ripe: Red
Flesh color full-ripe: Red/Crimson
Flesh color: With lighter and darker areas in walls
Locular gel color of table-ripe fruit: Red
Ripening: Blossom to stem end
Ripening: Uniformly
Stem scar size: Small (e.g., 'Roma')
Core: Coreless (absent or smaller than 6×6 mm)
Epidermis color: Yellow
Epidermis: Normal
Epidermis texture: Average
Thickness of the pericarp: 9.3 mm
Disease and Pest Reaction
Disease and Pest Reaction: Resistant to *verticillium* wilt race 1, *fusarium* wilt races 1 and 2, root knot nematode, early blight, bacterial spot, and bacterial canker
Chemistry and Composition of Full-Ripe Fruits

TABLE 2

|  | Variety 'H1307' | Check Variety 'H9553' | Check Variety 'H3402' |
|---|---|---|---|
| Soluble solids as ° Brix | 5.68 | 4.77 | 5.17 |
| Juice Bostwick | 11.9 | 12.4 | 12.2 |

Fruiting season: Medium (e.g., 'Westover')
Relative maturity in areas tested: Medium
Adaptation
Culture: Field
Principle use(s): Concentrated products
Machine harvest: Adapted
Regions to which adaptation has been demonstrated: Northeastern USA Further Embodiments Additional methods include, without limitation, chasing selfs. Chasing selfs involves identifying inbred plants among tomato plants that have been grown from hybrid tomato seed. Once the seed is planted, the inbred plants may be identified and selected due to their decreased vigor relative to the hybrid plants that grow from the hybrid seed, or by enzymatic or DNA patterns. By locating the inbred plants, isolating them from the rest of the plants, and self-pollinating them (i.e., "chasing selfs"), a breeder can obtain an inbred line that is identical to an inbred parent used to produce the hybrid.

Accordingly, another aspect of the present invention relates a method for producing an inbred tomato variety by: planting seed of the tomato variety 'H1307'; growing plants from the seed; identifying one or more inbred tomato plants; controlling pollination in a manner which preserves homozygosity of the one or more inbred plants; and harvesting resultant seed from the one or more inbred plants. The step of identifying the one or more inbred tomato plants may further include identifying plants with decreased vigor, i.e., plants that appear less robust than plants of the tomato variety 'H1307'. Tomato plants capable of expressing substantially all of the physiological and morphological characteristics of the parental inbred lines of tomato variety 'H1307' include tomato plants obtained by chasing selfs from seed of tomato variety '141307'.

One of ordinary skill in the art will recognize that once a breeder has obtained inbred tomato plants by chasing selfs from seed of tomato variety 'H1307', the breeder can then produce new inbred plants such as by sib-pollinating, or by crossing one of the identified inbred tomato plant with a plant of the tomato variety 'H1307'.

Deposit Information

A deposit of tomato variety 'H1307' is maintained by HeinzSeed Company, having an address at 6755 C. E. Dixon, Stockton, Calif. 95206, United States of America. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety 'H1307' will be irrevocably removed by affording access to a deposit of at least 2,500 seeds of the variety with the American Type Culture Collection, (ATCC), ATCC Patent Depository, 10801 University Boulevard, Manassas, Va., 20110, USA.

Tomato Variety 'H1307'

At least 2500 seeds of tomato variety 'H1307' were deposited on Apr. 18, 2017 according to the Budapest. Treaty in the American Type Culture Collection (ATCC), ATCC Patent Depository, 10801 University Boulevard, Manassas, Va., 20110, USA. The deposit has been assigned ATCC number PTA-124119. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed for the enforceable life of the patent.

The deposit will be maintained in the ATCC depository, which is a public depository, for a period of 30 years, or 5 years after the most recent request, or for the effective life of the patent, whichever is longer, and will be replaced if a deposit becomes nonviable during that period.

The invention claimed is:

1. Tomato seed designated as 'H1307', representative sample of seed having been deposited under ATCC Accession Number PTA-124119.

2. A plant produced by growing the seed of claim 1.

3. A plant part from the plant of claim 2, wherein the part is selected from the group consisting of leaves, ovules, pollen, tomato fruit, cotyledons, meristems, anthers, roots, root tips, pistils, flowers, stems, calli, stalks, hypocotyls, and pericarps.

4. The plant part of claim 3, wherein said part is tomato fruit.

5. A tomato plant having all the physiological and morphological characteristics of the tomato plant of claim 2.

6. A plant part from the plant of claim 5, wherein said, part is selected from the group consisting of leaves, ovules, pollen, tomato fruit, cotyledons, meristems, anthers, roots, root tips, pistils, flowers, stems, calli, stalks, hypocotyls, and pericarps.

7. The plant part of claim 6, wherein said part is tomato fruit.

8. Pollen of the plant of claim 2.

9. An ovule of the plant of claim 2.

10. A tissue culture of the plant of claim 2.

11. A method of making tomato seeds, the method comprising crossing the plant of claim 2 with another tomato plant and harvesting seed therefrom.

* * * * *

UNITED STATES PATENT AND TRADEMARK OFFICE
CERTIFICATE OF CORRECTION

PATENT NO. : 10,306,849 B2
APPLICATION NO. : 15/392765
DATED : June 4, 2019
INVENTOR(S) : George Collier Page 1 of 1

It is certified that error appears in the above-identified patent and that said Letters Patent is hereby corrected as shown below:

In the Claims

Column 6, Line 44, in Claim 6, delete "said," and insert --said--.

Signed and Sealed this
Thirty-first Day of March, 2020

Andrei Iancu
*Director of the United States Patent and Trademark Office*